(12) United States Patent  
Sasaki et al.

(10) Patent No.: US 12,223,144 B2
(45) Date of Patent: Feb. 11, 2025

(54) DETECTION DEVICE AND INFUSION PUMP

(71) Applicant: TERUMO KABUSHIKI KAISHA, Tokyo (JP)

(72) Inventors: Shohei Sasaki, Chigasaki (JP); Koji Hagi, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 189 days.

(21) Appl. No.: 17/939,905

(22) Filed: Sep. 7, 2022

(65) Prior Publication Data

US 2023/0004256 A1 Jan. 5, 2023

Related U.S. Application Data

(63) Continuation of application No. PCT/JP2021/007200, filed on Feb. 25, 2021.

(30) Foreign Application Priority Data

Mar. 11, 2020 (JP) ................................ 2020-042271

(51) Int. Cl.
*G06F 3/042* (2006.01)
(52) U.S. Cl.
CPC .......... *G06F 3/0425* (2013.01); *G06F 3/0421* (2013.01)
(58) Field of Classification Search
CPC .. G06F 3/0425; A61M 5/142; A61M 5/16831
See application file for complete search history.

(56) References Cited

U.S. PATENT DOCUMENTS

| 6,523,414 | B1 | 2/2003 | Malmstrom et al. |
| 8,054,452 | B2 * | 11/2011 | Bado ...................... G01N 21/85 |
| | | | 356/440 |
| 10,086,127 | B2 * | 10/2018 | Strohhöfer ............. G01N 21/94 |
| 2012/0280130 | A1 * | 11/2012 | Cummings ....... A61M 5/16831 |
| | | | 250/353 |
| 2016/0292866 | A1 | 10/2016 | Bloom et al. |
| 2017/0266378 | A1 | 9/2017 | Kamen et al. |

FOREIGN PATENT DOCUMENTS

| CN | 1933774 A | 3/2007 |
| CN | 101201605 A | 6/2008 |
| CN | 104602726 A | 5/2015 |
| IL | 195396 A | 12/2012 |

(Continued)

OTHER PUBLICATIONS

Extended European Search Report issued in connection with EP Appl. No. 21767345.8 dated Jul. 11, 2023.

(Continued)

*Primary Examiner* — Tarifur R Chowdhury
*Assistant Examiner* — Roberto Fabian, Jr.
(74) *Attorney, Agent, or Firm* — Foley & Lardner LLP

(57) ABSTRACT

A detection device according to the present disclosure includes: an irradiation unit configured to emit an infrared ray toward an infusion tube; an imaging unit configured to generate a captured image obtained by imaging the infusion tube irradiated with the infrared ray by the irradiation unit; and a control unit configured to detect blockage of the infusion tube and air bubbles in the infusion tube based on a light intensity distribution in the captured image.

17 Claims, 11 Drawing Sheets

(56) References Cited

FOREIGN PATENT DOCUMENTS

| | | |
|---|---|---|
| JP | H08-319131 A | 12/1996 |
| JP | 2011-206210 A | 10/2011 |
| JP | 2013-502979 A | 1/2013 |
| JP | 5837318 B2 | 12/2015 |
| JP | 2018-033957 A | 3/2018 |
| JP | 2019-163959 A | 9/2019 |
| KR | 2017-0034994 A | 3/2017 |
| KR | 101949705 B1 * | 2/2019 |
| WO | WO-2017/111077 A1 | 6/2017 |

OTHER PUBLICATIONS

Office Action issued in connection with Chinese Appl. No. 202180020593.6 dated Jun. 6, 2023.
International Searching Authority, "International Search Report," issued in connection with International Patent Application No. PCT/JP2021/007200, dated Apr. 13, 2021.
International Searching Authority, "Written Opinion," issued in connection with International Patent Application No. PCT/JP2021/007200, dated Apr. 13, 2021.
International Searching Authority, "Written Opinion," issued in connection with International Patent Application No. PCT/JP2021/007200, dated Apr. 13, 2021 with English translation.

* cited by examiner

FIG. 1
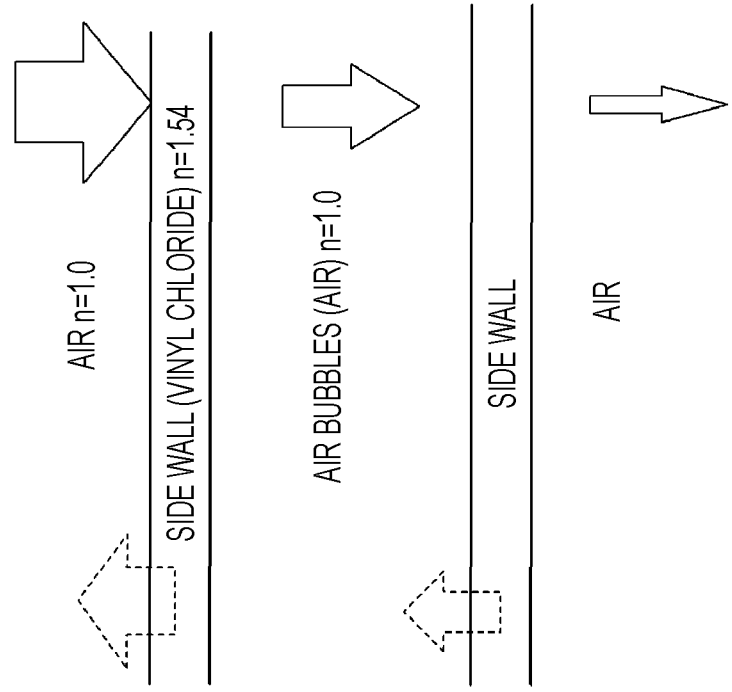
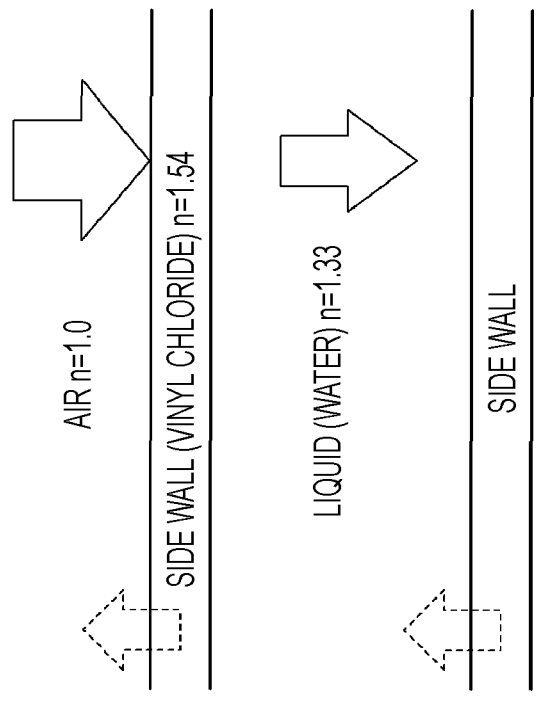

FIG. 4
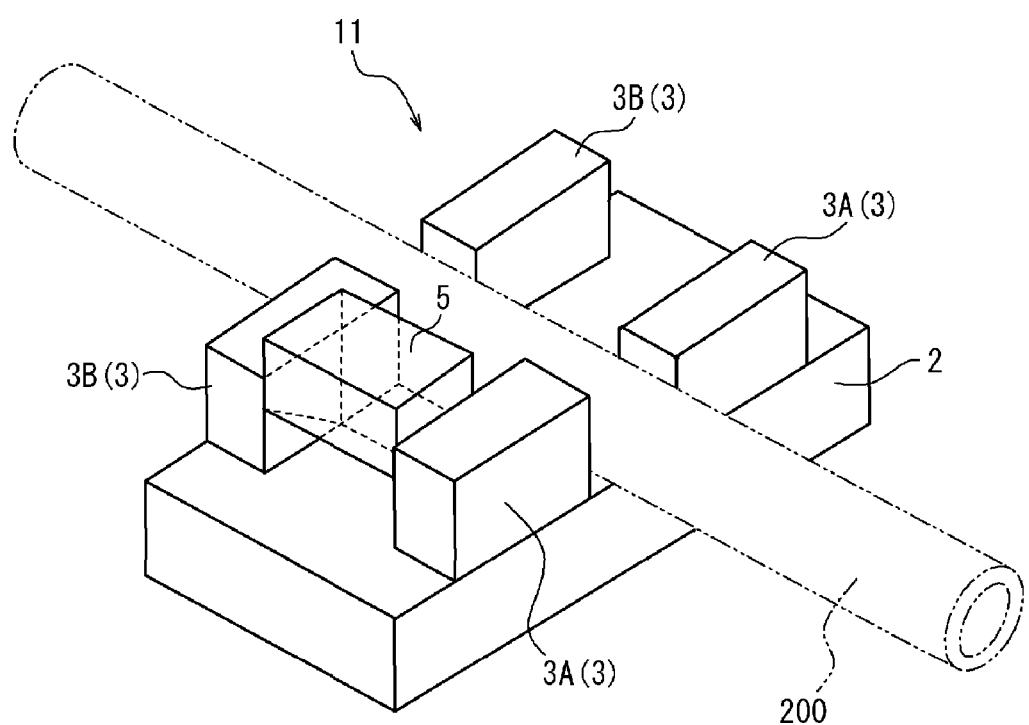
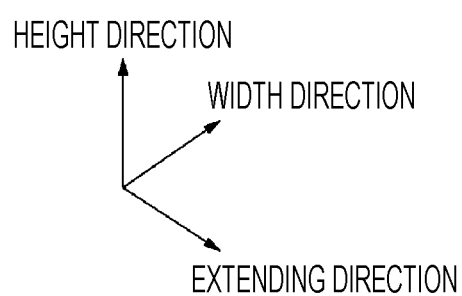

DETECTION DEVICE AND INFUSION PUMP

CROSS-REFERENCE TO RELATED APPLICATIONS

This is a bypass continuation of PCT Application No. PCT/JP2021/007200, filed on Feb. 25, 2021, which claims priority to Japanese Application No. JP2020-042271, filed on Mar. 11, 2020. The entire contents of these applications are hereby incorporated by reference.

BACKGROUND

The present disclosure relates to a detection device and an infusion pump.

Conventionally, a technique for detecting abnormality of an infusion tube when a medicinal solution is administered to a patient by an infusion pump is known. For example, Japanese Patent No. 5837318 B2 ("JP '318") discloses an infusion pump that detects blockage of an infusion tube using a Hall element. Japanese Patent Publication No. 2011-206210 A ("JP '210") discloses an infusion pump that detects air bubbles in an infusion tube using an ultrasonic sensor.

SUMMARY

In recent years, a reduction in size or weight is required for an infusion pump, such as a patient controlled analgesia (PCA) pump that can be carried by a patient and can be administered and adjusted by the patient himself/herself. Therefore, there is still room for improvement in such a device in terms of size and weight, and also in terms of a technique for detecting abnormality of an infusion tube as described in JP '318 and JP '210.

Embodiments of the present disclosure have been developed in view of such circumstances, and an object of certain embodiments is to provide a detection device and an infusion pump that improve a technique for detecting abnormality of an infusion tube.

A detection device according to an embodiment of the present disclosure includes: an irradiation unit configured to emit an infrared ray toward an infusion tube; an imaging unit configured to generate a captured image obtained by imaging the infusion tube irradiated with the infrared ray by the irradiation unit; and a control unit configured to detect blockage of the infusion tube and air bubbles in the infusion tube based on a light intensity distribution in the captured image.

In a detection device according to an embodiment of the present disclosure, the control unit is configured to detect blockage of the infusion tube based on an outer diameter of the infusion tube captured in the captured image.

In a detection device according to an embodiment of the present disclosure, the control unit is configured to detect air bubbles in the infusion tube based on a width of a region including a side wall of the infusion tube captured in the captured image.

In a detection device according to an embodiment of the present disclosure, the irradiation unit includes a first light source and a second light source that emit infrared rays toward the infusion tube from directions facing each other in a radial direction of the infusion tube, and the control unit is configured to detect blockage of the infusion tube and air bubbles in the infusion tube based on a captured image obtained by imaging the infusion tube in a state in which the infrared rays are emitted from both the first light source and the second light source.

In a detection device according to an embodiment of the present disclosure, the irradiation unit includes a plurality of light sources that emits infrared rays toward the infusion tube from different directions, and the control unit is configured to detect blockage of the infusion tube and air bubbles in the infusion tube based on a plurality of captured images obtained by imaging the infusion tube in a state in which the infrared rays are emitted from different light sources.

A detection device according to an embodiment of the present disclosure further includes a contact portion that comes into contact with the infusion tube from both sides of the infusion tube in a radial direction at two locations spaced apart from each other in an extending direction of the infusion tube, and the control unit is configured to detect blockage of the infusion tube and air bubbles in the infusion tube based on a light intensity distribution between the two locations in the extending direction of the infusion tube captured in the captured image.

An infusion pump according to an embodiment of the present disclosure includes the above-described detection device.

A detection device and an infusion pump according to the present disclosure can improve a technique for detecting abnormality of an infusion tube.

BRIEF DESCRIPTION OF THE DRAWINGS

FIG. 1 is a schematic diagram illustrating a path of an infrared ray emitted from the outside of an infusion tube in a radial direction toward the infusion tube.

FIG. 4 is a perspective view of a first housing of the detection device illustrated in FIG. 1.

DETAILED DESCRIPTION (Detection Device)

Figure 2:
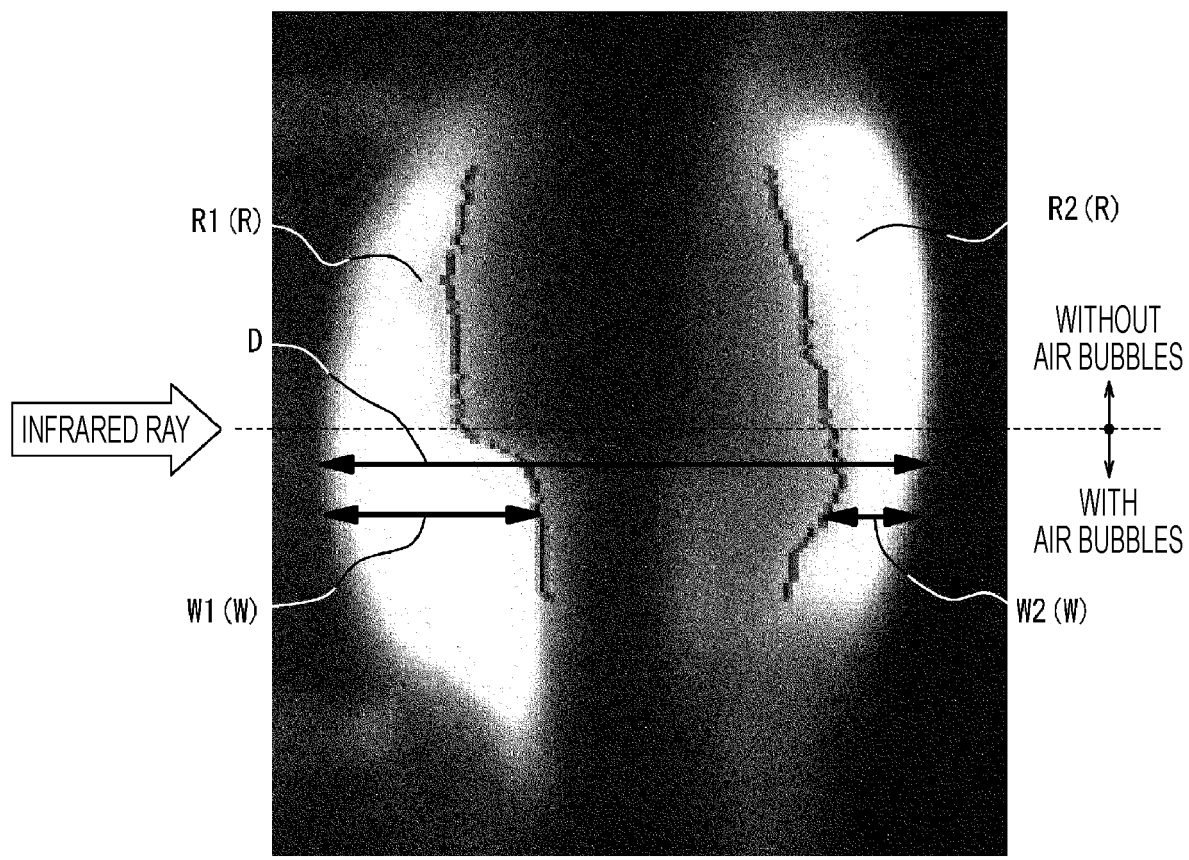
FIG. 2 is an example of a captured image of an infusion tube captured by a detection device according to an embodiment of the present disclosure.

Hereinafter, a detection device according to embodiments of the present disclosure will be described with reference to the drawings.

In the drawings, the same or corresponding parts are denoted by the same reference characters. In the description of the present embodiment, redundant descriptions of the same or corresponding parts will be omitted or simplified appropriately.

First, an outline of an operation of abnormality detection of an infusion tube by a detection device according to the present disclosure will be described with reference to FIGS. 1 and 2.

Although details will be described below, the detection device according to the present disclosure irradiates an infusion tube attached to the detection device with an infrared ray, receives an infrared ray reflected by the infusion tube, and generates a captured image obtained by imaging the infusion tube. The detection device detects blockage of the infusion tube and air bubbles in the infusion tube based on the generated captured image.

FIG. 1 is a schematic diagram illustrating a path of an infrared ray emitted from the outside of the infusion tube in a width direction toward the infusion tube. In FIG. 1, a solid or broken arrow indicates an infrared ray, and the thickness of the arrow indicates the intensity of the infrared ray. Furthermore, the solid arrow indicates incident light and transmitted light of an infrared ray emitted toward the infusion tube, and the broken arrow indicates an infrared ray reflected by the infusion tube. As illustrated in FIG. 1, an infrared ray emitted from the outside of the infusion tube in a width direction toward the infusion tube travels in the order of air outside the infusion tube, a side wall of the infusion tube, a liquid or air bubbles in the infusion tube, a side wall of the infusion tube, and air outside the infusion tube. At this time, a part of the infrared ray passes through a boundary between substances having different refractive indexes, and the other part of the infrared ray is reflected at the boundary between the substances having different refractive indexes. As an example, it is assumed that the side wall of the infusion tube, the liquid in the infusion tube, and the air bubbles in the infusion tube are vinyl chloride, water, and air, respectively. In this case, the refractive indexes of the side wall of the infusion tube, the liquid in the infusion tube, and the air bubbles in the infusion tube are, for example, 1.54, 1.33, and 1.0, respectively. Since the refractive index of the side wall of the infusion tube is larger than the refractive index of each of the other substances, a larger amount of the infrared ray is reflected at the boundary between the side wall of the infusion tube and each of the other substances.

FIG. 2 is an example of a captured image of the infusion tube captured by the detection device. The captured image illustrated in FIG. 2 is captured in a state in which the infusion tube extending in the vertical direction of the drawing is irradiated with an infrared ray from the left side in the horizontal direction of the drawing. In the present embodiment, in the captured image captured by the detection device, a portion where the intensity of the received infrared ray is high is bright, and conversely, a portion where the intensity of the received infrared ray is low is dark. Therefore, in the captured image, a region including both side walls of the infusion tube is displayed brightly in the extending direction of the captured infusion tube.

For example, the detection device can measure a light intensity value of each pixel included in the captured image by an image process such as an edge detection process, and can specify a high light intensity region R having a light intensity value equal to or more than a predetermined threshold as a region including both side walls of the infusion tube captured in the captured image based on a light intensity distribution in the captured image.

The detection device determines whether or not the infusion tube is blocked based on a light intensity distribution in the captured image. Specifically, when the infusion tube is blocked, the amount of liquid flowing in the infusion tube changes, and the thickness of the infusion tube changes. For example, when blockage occurs on a downstream side of a portion of the infusion tube captured in the captured image, the internal pressure of the portion increases, and the infusion tube captured in the captured image becomes thicker. Meanwhile, when the blockage occurs on an upstream side of the portion captured in the captured image of the infusion tube, the amount of liquid flowing in the portion decreases, and the internal pressure of the portion decreases. As a result, the infusion tube captured in the captured image becomes thinner.

Therefore, the detection device can determine whether or not the infusion tube is blocked based on the outer diameter D of the infusion tube captured in the captured image.

The detection device can further determine whether or not there are air bubbles in the infusion tube based on a light intensity distribution in the captured image. The captured image illustrated in FIG. 2 is captured in a state in which there is no air bubble in the infusion tube above a broken line and there are air bubbles in the infusion tube below the broken line. In the infusion tube, the light intensity distribution in the captured image is different between the portion where there are air bubbles inside and the portion where there is no air bubble inside due to a difference in refractive index between water and air. Specifically, as illustrated in FIG. 1, in a case where there are air bubbles inside, the intensity of a reflected infrared ray increases when the infrared ray is incident on the inside of the infusion tube from the side wall of the infusion tube as compared with a case where there is no air bubble inside. Therefore, as illustrated in FIG. 2, in the captured image, a region R1 of the infusion tube including a side wall on an infrared ray light source side is brighter and a width W1 thereof is thicker in the portion where there are air bubbles inside. Furthermore, in the portion where there are air bubbles inside, when the infrared ray is incident on the inside of the infusion tube from the side wall of the infusion tube, the intensity of the reflected infrared ray increases, and the intensity of transmitted infrared ray decreases. As described above, in the captured image, in the portion where there are air bubbles inside, a region R2 of the infusion tube including a side wall on a side opposite to the light source is darker and a width W2 thereof is thinner.

Therefore, the detection device can determine whether or not there are air bubbles in the infusion tube based on the width W (W1 or W2) of at least one of the regions R1 and R2 each including a side wall of the infusion tube captured in the captured image.

In the present embodiment, a captured image captured by the detection device is described on the assumption that a region where the intensity of a received infrared ray is high is bright, and a region where the intensity of the received infrared ray is low is dark. Therefore, the detection device specifies a high light intensity region having a light intensity value equal to or more than a predetermined threshold in the captured image as a region including both side walls of the infusion tube captured in the captured image. However, in the captured image, a region where the intensity of the received infrared ray is high may be displayed darkly, and a region where the intensity of the received infrared ray is low may be displayed brightly. In such a case, the detection device may specify a low light intensity region having a light intensity value equal to or less than a predetermined threshold in the captured image as a region including both side walls of the infusion tube captured in the captured image.

Figure 3:
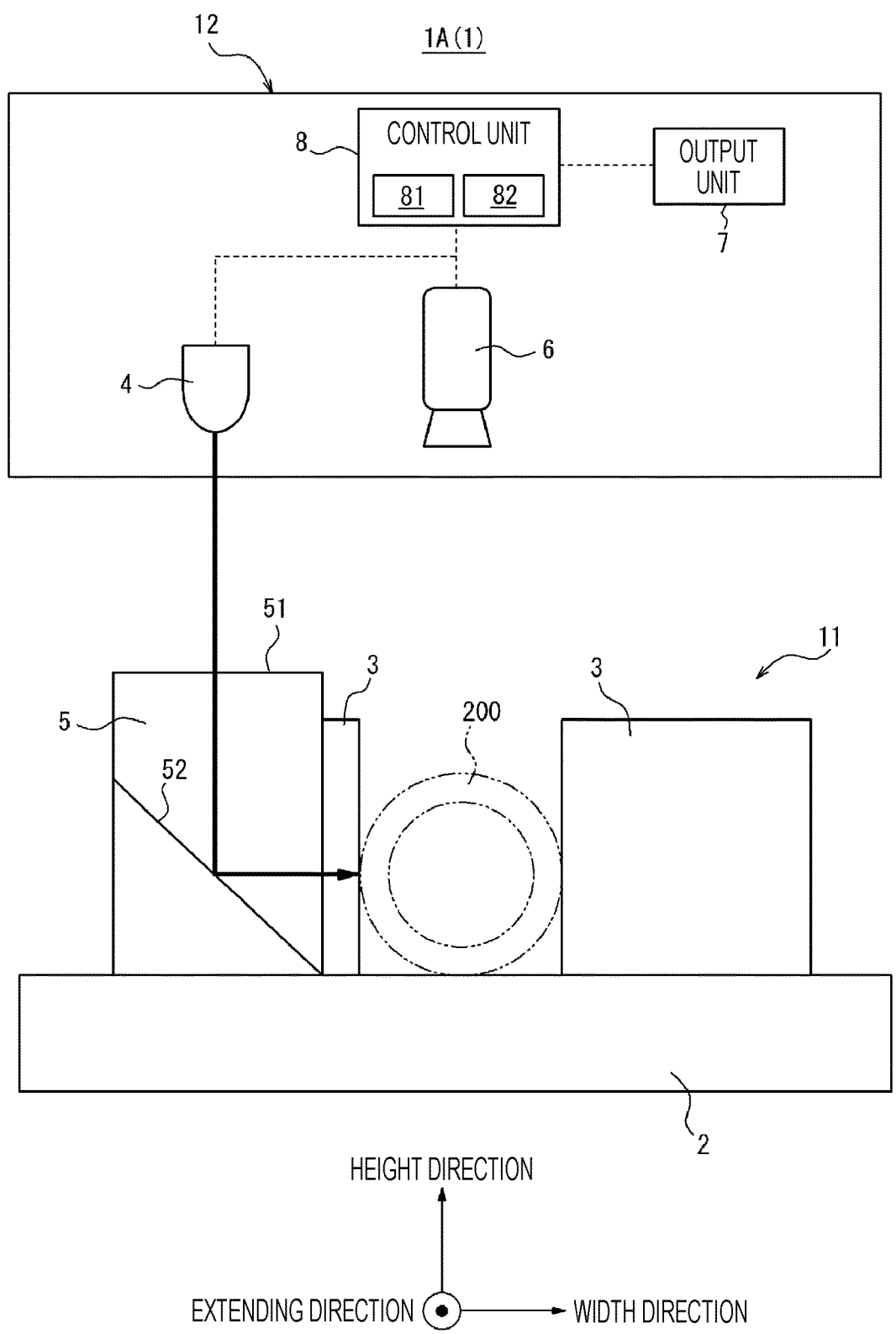
FIG. 3 is a schematic diagram illustrating a schematic configuration of a detection device according to a first embodiment of the present disclosure.

Next, a configuration of a detection device 1A, which is a first embodiment of the detection device according to the present disclosure, will be described in detail with reference to FIGS. 3 and 4. FIG. 3 is a schematic diagram illustrating a schematic configuration of the detection device 1A according to the first embodiment of the present disclosure. FIG. 4 is a perspective view of a first housing 11 of the detection device 1A. In FIG. 3, an infusion tube 200 attached to the detection device 1A is indicated by a two-dot chain line. The detection device 1A includes a receiving plate 2, a contact portion 3, an irradiation unit 4, a light guide 5, an imaging unit 6, an output unit 7, and a control unit 8. In the present embodiment, as illustrated in FIG. 3, the detection device 1A includes the first housing 11 to which the infusion tube 200 is attached, and a second housing 12 facing the first housing 11 with the infusion tube 200 interposed therebetween. In the detection device 1A, the receiving plate 2, the contact portion 3, and the light guide 5 are disposed in the first housing 11, and the irradiation unit 4, the imaging unit 6, the output unit 7, and the control unit 8 are disposed in the second housing 12.

The receiving plate 2 is formed of a plate-like member. A surface of the receiving plate 2 abuts on the infusion tube 200 when the infusion tube 200 is attached to the detection device 1A. In the present disclosure, as illustrated in FIG. 3, a direction in which the infusion tube 200 attached to the detection device 1A extends is referred to as an extending direction. A direction orthogonal to the extending direction on the surface of the receiving plate 2 is referred to as a width direction. A direction orthogonal to the extending direction and the width direction is referred to as a height direction. Furthermore, in the infusion tube 200, a direction orthogonal to the extending direction is referred to as a radial direction. The radial direction of the infusion tube 200 includes the width direction and the height direction of the infusion tube 200.

The contact portion 3 is configured to come into contact with the infusion tube 200 from both sides of the infusion tube 200 in the radial direction at two locations spaced apart from each other in the extending direction of the infusion tube 200 attached to the detection device 1A. As illustrated in FIG. 4, the contact portion 3 includes a first contact portion 3A and a second contact portion 3B. The first contact portion 3A and the second contact portion 3B protrude from the receiving plate 2 in the height direction at positions spaced apart from each other in the extending direction of the infusion tube 200 on the surface of the receiving plate 2. Each of the first contact portion 3A and the second contact portion 3B includes two protrusions facing each other so as to come into contact with the infusion tube 200 from both sides of the infusion tube 200 in the width direction. As a result, in the infusion tube 200 attached to the detection device 1A, the shape of the side wall is likely to change according to the amount of infusion flowing inside between the two locations in contact with the first contact portion 3A and the second contact portion 3B. Therefore, the detection device 1A can more accurately detect abnormality of the infusion tube 200 by detecting abnormality between the two locations in contact with the first contact portion 3A and the second contact portion 3B of the infusion tube 200. Hereinafter, a "section between the two locations in contact with the first contact portion 3A and the second contact portion 3B" of the infusion tube 200 is also referred to as a "target section" of the infusion tube 200.

Referring again to FIG. 3, the irradiation unit 4 is configured to emit an infrared ray toward the infusion tube 200 attached to the detection device 1A. More specifically, the irradiation unit 4 is configured to emit an infrared ray toward the target section of the infusion tube 200. The irradiation unit 4 includes one or more light sources. The light source is, for example, an infrared ray light emitting diode (LED). In the present embodiment, the irradiation unit 4 is disposed at a position of the second housing 12 where an incident surface 51 of the light guide 5 disposed in the first housing 11 can be irradiated with an infrared ray.

The light guide 5 is configured to guide an infrared ray emitted from the irradiation unit 4 to the infusion tube 200 attached to the detection device 1A. The light guide 5 is, for example, an acrylic light guide member. In the present embodiment, the light guide 5 includes the incident surface 51 on which an infrared ray emitted from the irradiation unit 4 is incident and a reflecting surface 52 located on a side opposite to the incident surface 51 in the height direction. The reflecting surface 52 is an inclined surface having a predetermined inclination with respect to the height direction. In the present embodiment, the light guide 5 is disposed at a position sandwiched between the first contact portion 3A and the second contact portion 3B in the extending direction and facing the irradiation unit 4 in the height direction in the first housing 11. As a result, as indicated by an arrow in FIG. 3, an infrared ray emitted from the irradiation unit 4 in the height direction is incident on the incident surface 51 of the light guide 5, is reflected by the reflecting surface 52, travels in the width direction, and is emitted to the infusion tube 200 from the width direction of the infusion tube 200 attached to the detection device 1A. In the present embodiment, an infrared ray emitted from the irradiation unit 4 is emitted to the target section of the infusion tube 200 attached to the detection device 1A from the width direction of the infusion tube 200 via the light guide 5.

By disposing the light guide 5 in the first housing 11, the irradiation unit 4 can be disposed in the second housing 12 different from the first housing 11 to which the infusion tube 200 is attached. In the present embodiment, by disposing, in addition to the irradiation unit 4, relatively expensive components such as the imaging unit 6, the output unit 7, and the control unit 8 in the second housing 12, for example, when the infusion tube 200 is damaged, only the first housing 11 that can be contaminated with liquid in the infusion tube 200 can be replaced, and the second housing 12 can be continuously used.

The imaging unit 6 is configured to generate a captured image obtained by imaging the infusion tube 200 attached to the detection device 1A. More specifically, the imaging unit 6 generates a captured image obtained by imaging the target section of the infusion tube 200. The imaging unit 6 receives an infrared ray emitted from the irradiation unit 4 and reflected by the infusion tube 200. As a result, the imaging unit 6 can generate a captured image obtained by imaging the infusion tube 200 irradiated with an infrared ray from the irradiation unit 4. The imaging unit 6 includes an image sensor. The image sensor is, for example, a complementary metal oxide semiconductor (CMOS) image sensor, or a charge-coupled device (CCD) image sensor. In the present embodiment, the imaging unit 6 is disposed at a position of the second housing 12 facing the infusion tube 200 attached to the detection device 1A in the height direction.

The output unit 7 is configured to output sound, vibration, light, an image, or the like. The output unit 7 includes, for example, an output device such as a speaker, a vibrator, a lamp, or a display.

The control unit 8 includes, for example, a memory 81 and a processor 82.

The memory 81 is, for example, a semiconductor memory, a magnetic memory, or an optical memory. The memory 81 functions as, for example, a main storage device, an auxiliary storage device, or a cache memory. The memory 81 stores arbitrary information used for an operation of the detection device 1A. For example, the memory 81 stores a system program, an application program, or embedded software.

The processor 82 may be, for example, a general-purpose processor such as a central processing unit (CPU) or a dedicated processor specialized for a specific process. The processor 82 may include, for example, a dedicated circuit such as a field-programmable gate array (FPGA) or an application specific integrated circuit (ASIC).

The control unit 8 is connected to each of the irradiation unit 4, the imaging unit 6, and the output unit 7 so as to be able to communicate therewith in a wired or wireless manner. As a result, the control unit 8 controls each unit such as the irradiation unit 4, the imaging unit 6, or the output unit 7.

Figure 5:
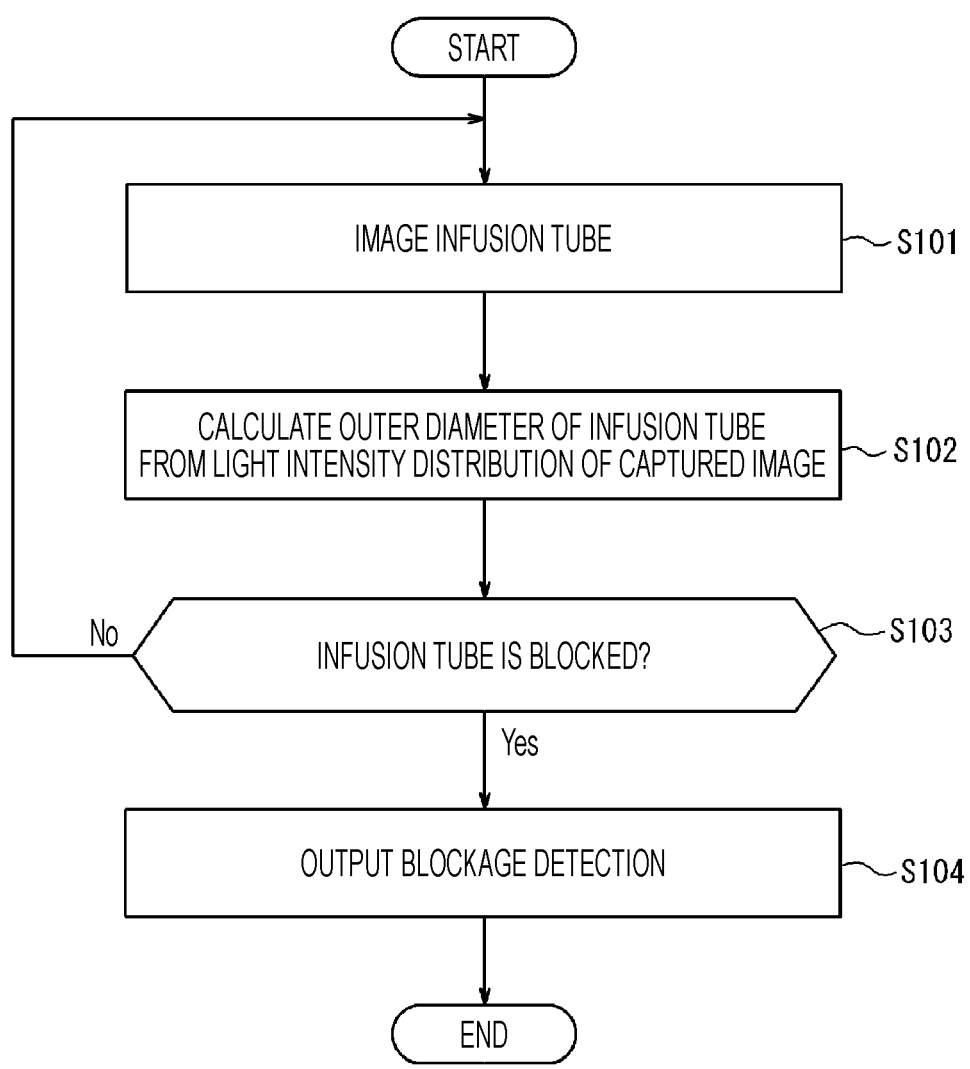
FIG. 5 is a flowchart illustrating an operation of blockage detection by the detection device illustrated in FIG. 1.
Figure 6:
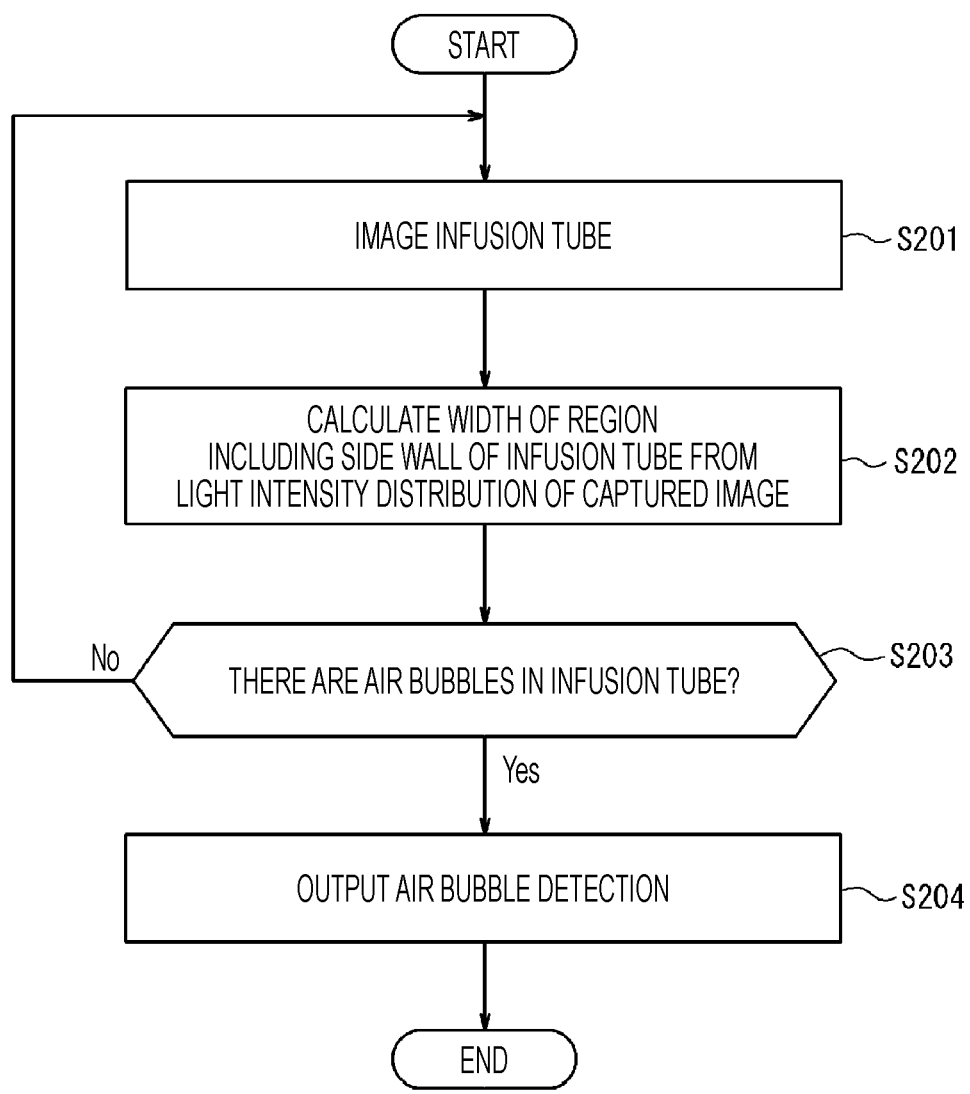
FIG. 6 is a flowchart illustrating an operation of air bubble detection by the detection device illustrated in FIG. 1.

The control unit 8 detects blockage of the infusion tube 200 and air bubbles in the infusion tube 200 based on a light intensity distribution in a captured image. An operation of the detection device 1A according to the present embodiment under control of the control unit 8 will be described with reference to FIGS. 5 and 6. FIG. 5 is a flowchart illustrating an operation of blockage detection by the detection device 1A. FIG. 6 is a flowchart illustrating an operation of air bubble detection by the detection device 1A. These operations correspond to a detection method executed by the detection device 1A. These operations will be described as being executed in a state in which the infusion tube 200 is attached to the detection device 1A.

(Blockage Detection)

First, an operation of blockage detection by the detection device 1A will be described with reference to FIG. 5.

Step S101: The detection device 1A images the infusion tube 200.

Specifically, the control unit 8 causes the irradiation unit 4 to irradiate the infusion tube 200 with an infrared ray from the width direction of the infusion tube 200 attached to the detection device 1A. The control unit 8 causes the imaging unit 6 to image the infusion tube 200 and generate a captured image in a state in which the infusion tube 200 is irradiated with the infrared ray. The control unit 8 may store the captured image generated by the imaging unit 6.

Step S102: The detection device 1A measures the outer diameter D of the infusion tube 200 captured in the captured image at least at one point of the infusion tube 200 captured in the captured image in the extending direction based on a light intensity distribution.

Specifically, the control unit 8 specifies a high light intensity region R (see FIG. 2) having a light intensity value equal to or more than a predetermined threshold in the captured image by an edge detection process. The high light intensity region R includes a first region R1 and a second region R2 distributed in the extending direction of the infusion tube 200 captured in the captured image. The first region R1 is a region including one of the two side walls of the infusion tube 200 captured in the captured image. The second region R2 is a region including a side wall different from the first region R1 out of the two side walls of the infusion tube 200 captured in the captured image. In the present embodiment, the control unit 8 measures a distance between the farthest ends of the first region R1 and the second region R2 at a certain point of the infusion tube 200 in the extending direction captured in the captured image. The control unit 8 stores the measured distance between the farthest ends of the first region R1 and the second region R2 as the outer diameter D of the infusion tube 200. However, the control unit 8 may measure a distance between the farthest ends of the first region R1 and the second region R2 at a plurality of points of the infusion tube 200 in the extending direction captured in the captured image. In such a case, the control unit 8 may define an average value, a maximum value, a minimum value, or the like of the outer diameter of the infusion tube 200 at each of the plurality of points of the infusion tube 200 in the extending direction captured in the captured image as the outer diameter D of the infusion tube 200. Furthermore, the control unit 8 stores the outer diameter D of the infusion tube 200 measured by first executing step S102 as an initial value $D_0$.

Step S103: The detection device 1A determines whether or not the infusion tube 200 is blocked based on the measured outer diameter D of the infusion tube 200.

Specifically, the control unit 8 determines whether or not the measured outer diameter D of the infusion tube 200 and its initial value $D_0$ satisfy the following formula (1).

$$D_A < D - D_0 < D_B \qquad \text{Formula (1)}$$

Here, $D_A$ and $D_B$ are thresholds for blockage detection. $D_A$ and $D_B$ are an upper limit value and a lower limit value of a displacement of the measured outer diameter D of the infusion tube 200 from the initial value $D_0$, respectively. In the present embodiment, $D_A$ is a negative constant, and $D_B$ is a positive constant.

When the measured outer diameter D of the infusion tube 200 satisfies formula (1), that is, when a displacement of the outer diameter D from the initial value $D_0$ is within a predetermined range, the control unit 8 determines that the infusion tube 200 is not blocked. When the control unit 8 determines that the infusion tube 200 is not blocked (step S103—No), the control unit 8 continues the process from step S101.

When the measured outer diameter D of the infusion tube 200 does not satisfy formula (1), that is, when a displacement of the outer diameter D from the initial value $D_0$ is not within a predetermined range, the control unit 8 determines that the infusion tube 200 is blocked. When the control unit 8 determines that the infusion tube 200 is blocked (step S103—Yes), the control unit 8 executes a process of step S104.

Step S104: The detection device 1A outputs that blockage of the infusion tube 200 has been detected.

Specifically, the control unit 8 causes the output unit 7 to output that blockage of the infusion tube 200 has been detected, and ends the present process. For example, the control unit 8 may cause a display included in the output unit 7 to display "blockage detection".

The control unit 8 may further change the output content to be output by the output unit 7 according to a detected state of blockage of the infusion tube 200.

For example, when $D_A$ $D-D_0$ is satisfied, the control unit 8 determines that the outer diameter D of the infusion tube 200 captured in the captured image is narrower than the initial value $D_0$ by a predetermined amount or more. This is considered to be because the amount of liquid flowing through the infusion tube 200 captured in the captured image has decreased due to occurrence of blockage on an upstream side of the infusion tube 200 captured in the captured image. In such a case, the control unit 8 may cause the output unit 7 to output that blockage has occurred on the upstream side of the infusion tube 200 captured in the captured image.

For example, when $D_B$ D–$D_0$ is satisfied, the control unit 8 determines that the outer diameter D of the infusion tube 200 captured in the captured image is wider than the initial value $D_0$ by a predetermined amount or more. This is considered to be because the amount of liquid flowing through the infusion tube 200 captured in the captured image has increased due to occurrence of blockage on a downstream side of the infusion tube 200 captured in the captured image. In such a case, the control unit 8 may cause the output unit 7 to output that blockage has occurred on the downstream side of the infusion tube 200 captured in the captured image.

(Air Bubble Detection)

Next, an operation of air bubble detection by the detection device 1A will be described with reference to FIG. 6. In the present embodiment, an example will be described in which the detection device 1A measures both the widths W1 and W2 of the region including the side wall of the infusion tube 200 captured in the captured image to perform air bubble detection. However, the detection device 1A may measure one of the widths W1 and W2 to perform air bubble detection. In such a case, in the description of subsequent steps, a process for the other width W1 or W2 that has not been measured is not performed.

Step S201: The detection device 1A images the infusion tube 200 as described in step S101.

Specifically, the control unit 8 causes the irradiation unit 4 to irradiate the infusion tube 200 with an infrared ray from the width direction of the infusion tube 200 attached to the detection device 1A. The control unit 8 causes the imaging unit 6 to image the infusion tube 200 and generate a captured image in a state in which the infusion tube 200 is irradiated with the infrared ray. The control unit 8 may store the captured image generated by the imaging unit 6.

Step S202: The detection device 1A measures the width W of the region including the side wall of the infusion tube 200 captured in the captured image at least at one point of the infusion tube 200 in the extending direction captured in the captured image based on a light intensity distribution.

Specifically, the control unit 8 specifies a high light intensity region R having a light intensity value equal to or more than a predetermined threshold in the captured image by an edge detection process. As described above, the high light intensity region R includes the first region R1 and the second region R2 including the two side walls of the infusion tube 200, respectively. In the present embodiment, the control unit 8 measures the width W1 of the first region R1 and the width W2 of the second region R2 at a certain point of the infusion tube 200 in the extending direction captured in the captured image. However, the control unit 8 may measure the widths of the first region R1 and the second region R2 at a plurality of points of the infusion tube 200 in the extending direction captured in the captured image. In such a case, the control unit 8 may define average values, maximum values, minimum values, or the like of the widths of the first region R1 and the second region R2 at the plurality of points of the infusion tube 200 in the extending direction captured in the captured image as the width W1 of the first region R1 and the width W2 of the second region R2, respectively. Furthermore, the control unit 8 stores the width W1 of the first region R1 and the width W2 of the second region R2 measured by first executing step S202 as initial values $W1_0$ and $W2_0$, respectively.

Step S203: The detection device 1A determines whether or not air bubbles are generated in the infusion tube 200 based on the measured width W of the region including the side wall of the infusion tube 200.

Specifically, the control unit 8 determines whether or not the measured width W1 of the first region R1 and its initial value $W1_0$ satisfy the following formula (2).

$$W1 - W1_0 < W1_A \qquad \text{Formula (2)}$$

Here, $W1_A$ is a threshold for air bubble detection. $W1_A$ is an upper limit value of a displacement of the measured width W of the first region R1 of the infusion tube 200 from the initial value $W1_0$. In the present embodiment, $W1_A$ is a positive constant.

The control unit 8 further determines whether or not the measured width W2 of the second region R2 and its initial value $W2_0$ satisfy the following formula (3).

$$W2 - W2_0 < W2_A \qquad \text{Formula (3)}$$

Here, $W2_A$ is a threshold for air bubble detection. $W2_A$ is a lower limit value of a displacement of the measured width W of the second region R2 of the infusion tube 200 from the initial value $W2_0$. $W2_A$ is a negative constant.

When the measured width W1 of the first region R1 satisfies formula (2) and the measured width W2 of the second region R2 satisfies formula (3), that is, when displacements of the widths W1 and W2 from the initial values $W1_0$ and $W2_0$ are within the predetermined ranges, respectively, the control unit 8 determines that there is no air bubble in the infusion tube 200. When the control unit 8 determines that there is no air bubble in the infusion tube 200 (step S203-No), the control unit 8 continues the process from step S201.

When the measured width W1 of the first region R1 does not satisfy formula (2) or the measured width W2 of the second region R2 does not satisfy formula (3), that is, when at least one of displacements of the widths W1 and W2 from the initial values $W1_0$ and $W2_0$, respectively, is not within the predetermined range, the control unit 8 determines that there are air bubbles in the infusion tube 200. When the control unit 8 determines that there are air bubbles in the infusion tube 200 (step S203—Yes), the control unit 8 executes a process of step S204.

Step S204: The detection device 1A outputs that air bubbles in the infusion tube 200 have been detected.

Specifically, the control unit 8 causes the output unit 7 to output that air bubbles in the infusion tube 200 have been detected, and ends the present process. For example, the control unit 8 may cause a display included in the output unit 7 to display "air bubble detection".

In the present disclosure, the process of detecting blockage of the infusion tube 200 and the process of detecting air bubbles in the infusion tube 200 have been individually described, but these processes may be performed in parallel. Specifically, the control unit 8 performs the process of detecting blockage of the infusion tube 200 and the process of detecting air bubbles in the infusion tube 200 on one captured image captured by the imaging unit 6. When blockage of the infusion tube 200 is not detected and no air bubble in the infusion tube 200 is detected, the control unit 8 continues these processes. When blockage of the infusion tube 200 is detected or when air bubbles in the infusion tube 200 are detected, the control unit 8 may cause the output unit 7 to output the fact and end these processes.

(Second Embodiment of Detection Device)

Figure 7:
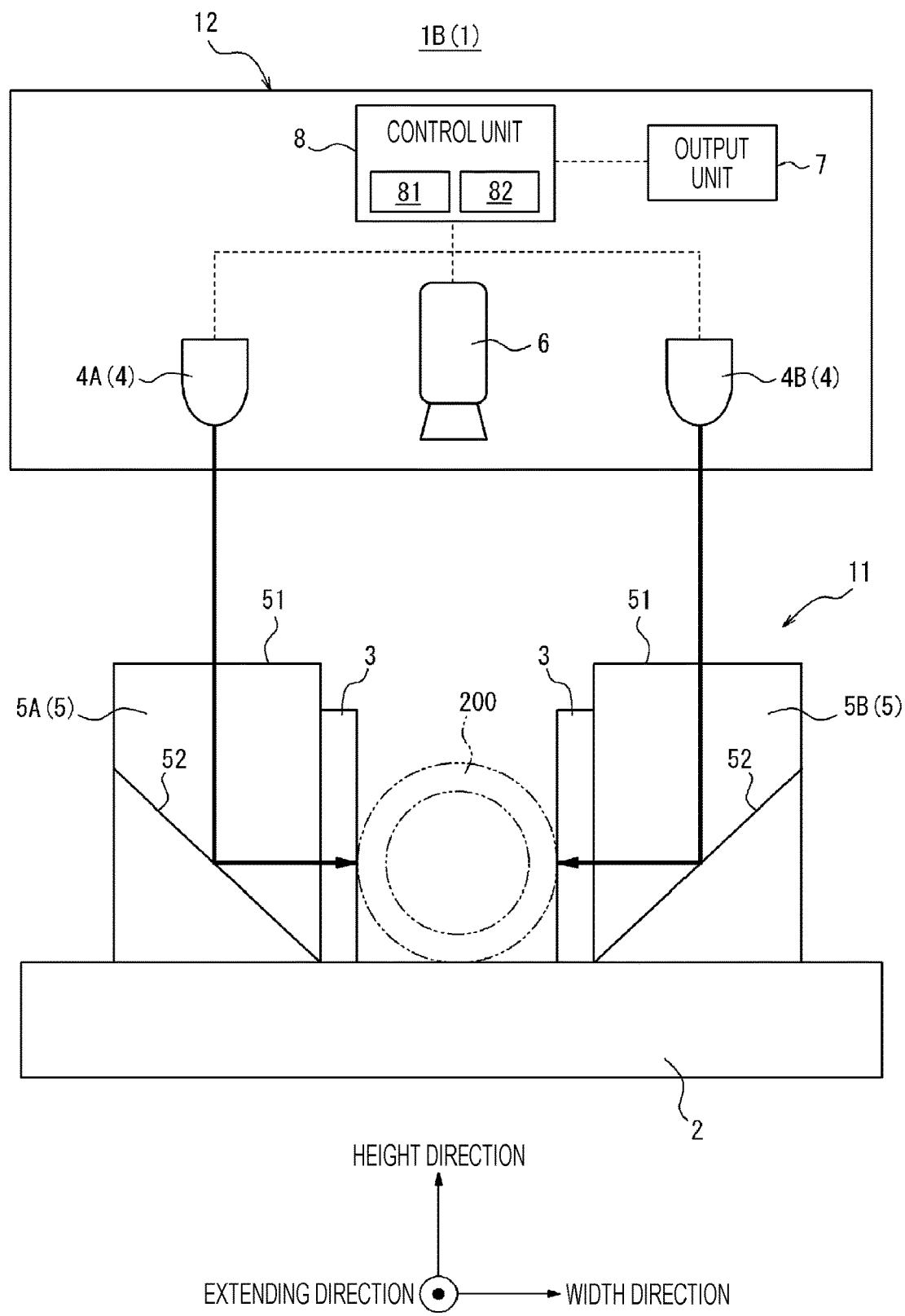
FIG. 7 is a schematic diagram illustrating a schematic configuration of a detection device according to a second embodiment of the present disclosure.

A detection device 1B, which is a second embodiment of the detection device according to the present disclosure, will be described with reference to FIG. 7. FIG. 7 is a schematic diagram illustrating a schematic configuration of the detection device 1B according to the second embodiment.

The detection device 1B is different from the detection device 1A described above in the first embodiment in that an irradiation unit 4 of the detection device 1B includes two light sources (for example, a first light source 4A and a second light source 4B) in the second embodiment. Furthermore, the detection device 1B is different from the detection device 1A in including two light guides 5. Hereinafter, the second embodiment will be described focusing on differences from the first embodiment. Note that portions having the same configurations as those of the first embodiment are denoted by the same reference characters.

As illustrated in FIG. 7, the detection device 1B includes a receiving plate 2, a contact portion 3, the irradiation unit 4, the light guide 5, an imaging unit 6, an output unit 7, and a control unit 8.

In the detection device 1B, the irradiation unit 4 includes the first light source 4A and the second light source 4B that emit infrared rays from directions facing each other in a radial direction of an infusion tube 200 attached to the detection device 1B toward the infusion tube 200. In the present embodiment, the first light source 4A and the second light source 4B of the irradiation unit 4 are disposed at positions of a second housing 12 where incident surfaces 51 of the two light guides 5A and 5B disposed in a first housing 11 can be irradiated with infrared rays, respectively.

The two light guides 5A and 5B may each have the same shape as the light guide 5 of the detection device 1A described above in the first embodiment. In the detection device 1B, the light guide 5A is disposed at the same position as the light guide 5 described above in the detection device 1A in the first housing 11. The light guide 5B is disposed at a position facing the light guide 5A with the infusion tube 200 attached to the detection device 1B interposed therebetween in the first housing 11. As a result, as indicated by an arrow in FIG. 7, an infrared ray emitted from the first light source 4A of the irradiation unit 4 in the height direction is emitted to the infusion tube 200 from the width direction of the infusion tube 200 via the light guide 5A. Furthermore, an infrared ray emitted from the second light source 4B of the irradiation unit 4 in the height direction is emitted to the infusion tube 200 from a direction facing the infrared ray emitted from the first light source 4A in the width direction of the infusion tube 200 via the light guide 5B.

The control unit 8 of the detection device 1B causes the irradiation unit 4 to emit infrared rays from both the first light source 4A and the second light source 4B. The control unit 8 of the detection device 1B causes the imaging unit 6 to capture a captured image obtained by imaging the infusion tube 200 in a state in which infrared rays are emitted from both the first light source 4A and the second light source 4B. The control unit 8 of the detection device 1B performs a process of detecting blockage of the infusion tube 200 and a process of detecting air bubbles in the infusion tube 200 in a similar manner to the method described above in the detection device 1A based on the captured image. When blockage of the infusion tube 200 or air bubbles in the infusion tube 200 are detected based on the captured image, the control unit 8 of the detection device 1B causes the output unit 7 to output the fact.

With such a configuration, the detection device 1B can irradiate the infusion tube 200 with infrared rays from two directions facing each other to more clearly image the infusion tube 200 as compared with a case where the infusion tube 200 is irradiated with an infrared ray from one direction. As a result, the detection device 1B can more accurately detect abnormality of the infusion tube 200.

(Third Embodiment of Detection Device)

Figure 8:
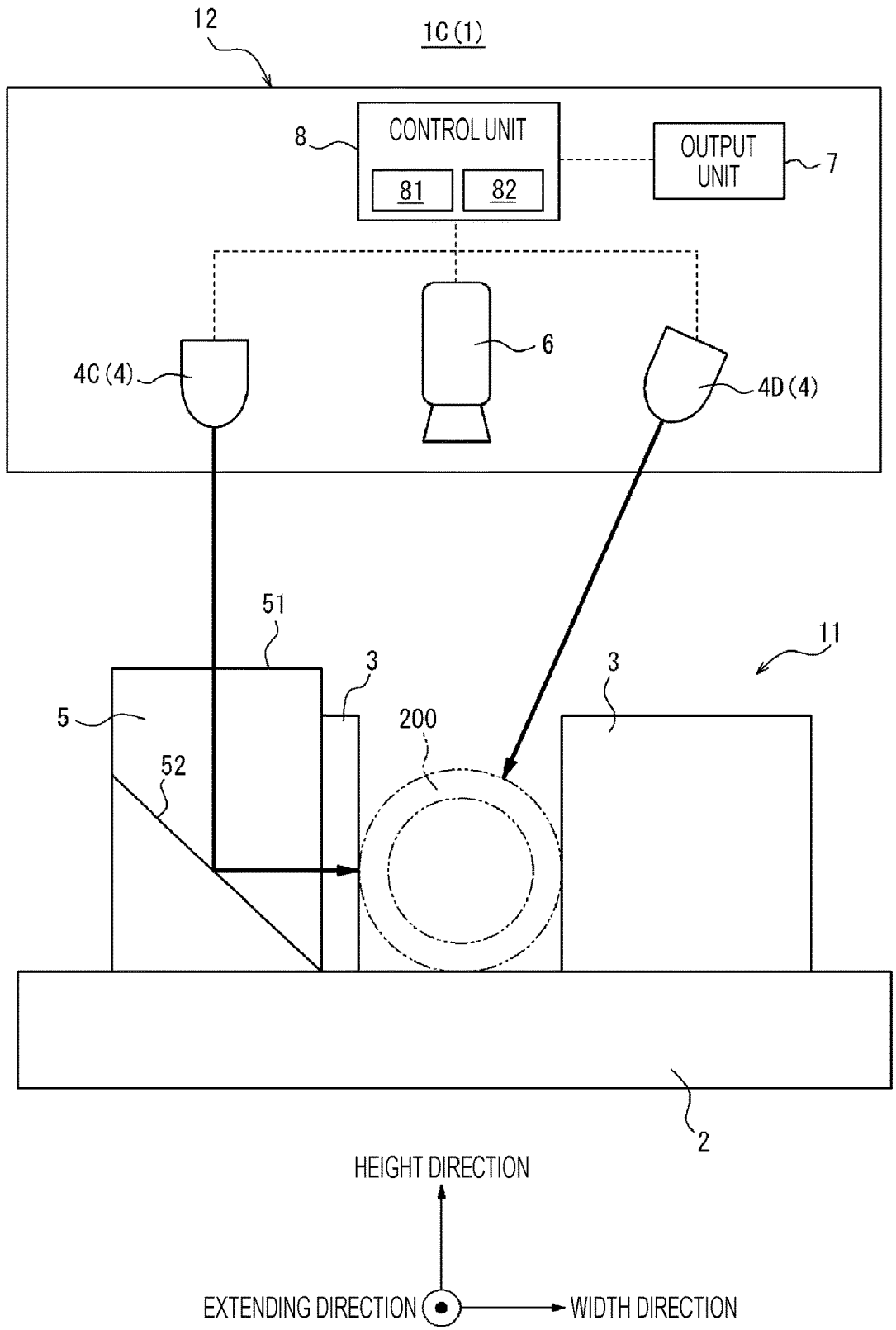
FIG. 8 is a schematic diagram illustrating a schematic configuration of a detection device according to a third embodiment of the present disclosure.

A detection device 1C, which is a third embodiment of the detection device according to the present disclosure, will be described with reference to FIG. 8. FIG. 8 is a schematic diagram illustrating a schematic configuration of the detection device 1C according to the third embodiment.

The detection device 1C is different from the detection device 1A described above in the first embodiment in that an irradiation unit 4 of the detection device 1C includes a plurality of light sources (for example, two light sources 4C and 4D) in the third embodiment. Hereinafter, the third embodiment will be described focusing on differences from the first embodiment. Note that portions having the same configurations as those of the first embodiment are denoted by the same reference characters.

As illustrated in FIG. 8, the detection device 1C includes a receiving plate 2, a contact portion 3, the irradiation unit 4, a light guide 5, an imaging unit 6, an output unit 7, and a control unit 8.

In the detection device 1C, the irradiation unit 4 includes the plurality of light sources 4C and 4D that emits infrared rays toward an infusion tube 200 from different directions. The present embodiment will be described on the assumption that the number of the plurality of light sources is two, but the number of the plurality of light sources may be three or more. In the present embodiment, the light source 4C of the irradiation unit 4 is disposed at the same position of the second housing 12 as the light source of the irradiation unit 4 described above in the detection device 1A. That is, the light source 4C is disposed at the position of the second housing 12 where the infusion tube 200 can be irradiated with an infrared ray from the width direction of the infusion tube 200 via the light guide 5 disposed in a first housing 11. Meanwhile, the light source 4D is disposed at a position of the second housing 12 where the infusion tube 200 attached to the detection device 1C can be directly irradiated with an infrared ray. That is, the light source 4D is disposed at the position of the second housing 12 where the infusion tube 200 can be irradiated with an infrared ray from a direction different from the light source 4C. As a result, as indicated by an arrow in FIG. 8, in the detection device 1C, the light source 4C of the irradiation unit 4 can irradiate the infusion tube 200 with an infrared ray from the width direction of the infusion tube 200. In addition, in the detection device 1C, the light source 4D of the irradiation unit 4 can irradiate the infusion tube 200 with an infrared ray from a direction different from the light source 4C.

The control unit 8 of the detection device 1C causes the irradiation unit 4 to emit infrared rays alternately from the plurality of light sources 4C and 4D. The control unit 8 of the detection device 1C causes the imaging unit 6 to capture a first captured image obtained by imaging the infusion tube 200 in a state in which an infrared ray is emitted from the light source 4C. The control unit 8 of the detection device 1C causes the imaging unit 6 to capture a second captured image obtained by imaging the infusion tube 200, for example, in a state in which an infrared ray is emitted from the light source 4D. The control unit 8 of the detection device 1C performs a process of detecting blockage of the infusion tube 200 and a process of detecting air bubbles in the infusion tube 200 in a similar manner to the method described above in the detection device 1A based on each of the first captured image and the second captured image. When blockage of the infusion tube 200 or air bubbles in the infusion tube 200 are detected based on at least one of the first captured image and the second captured image, the control unit 8 of the detection device 1C causes the output unit 7 to output the fact.

With such a configuration, the detection device 1C can irradiate the infusion tube 200 with infrared rays from various directions to image the infusion tube 200. As a result, the detection device 1C can more accurately detect abnormality of the infusion tube 200.

(Fourth Embodiment of Detection Device)

Figure 9:
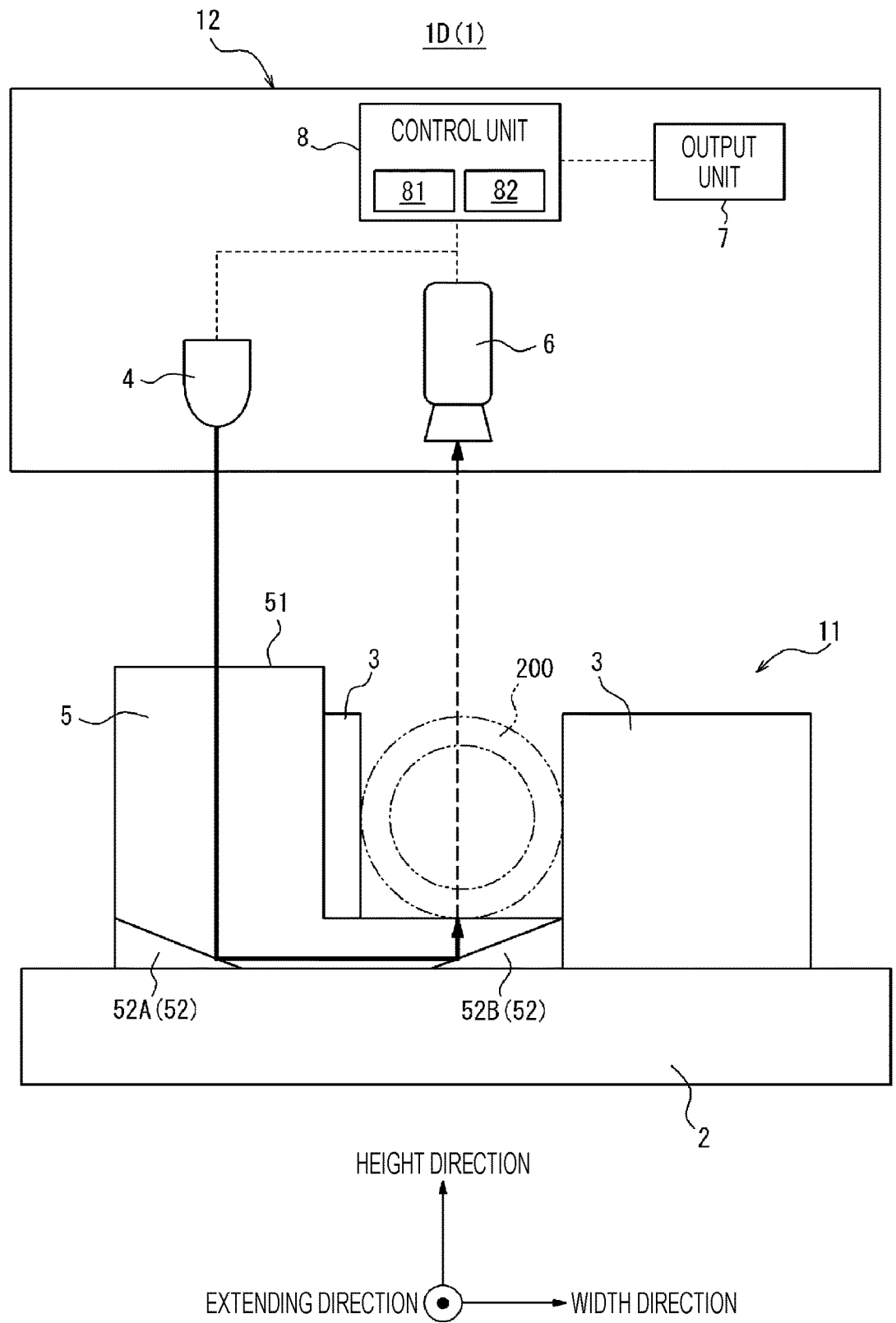
FIG. 9 is a schematic diagram illustrating a schematic configuration of a detection device according to a fourth embodiment of the present disclosure.

A detection device 1D, which is a fourth embodiment of the detection device according to the present disclosure, will be described with reference to FIG. 9. FIG. 9 is a schematic diagram illustrating a schematic configuration of the detection device 1D according to the fourth embodiment.

The detection device 1D is different from the detection device 1A described above in the first embodiment in that an infrared ray emitted from an irradiation unit 4 of the detection device 1D is emitted to an infusion tube 200 from a lower portion of the infusion tube 200 in the height direction toward an imaging unit 6 in the fourth embodiment. Hereinafter, the fourth embodiment will be described focusing on differences from the first embodiment. Note that portions having the same configurations as those of the first embodiment are denoted by the same reference characters.

As illustrated in FIG. 9, the detection device 1D includes a receiving plate 2, a contact portion 3, the irradiation unit 4, a light guide 5, the imaging unit 6, an output unit 7, and a control unit 8.

In the detection device 1D, the light guide 5 has an incident surface 51 on which an infrared ray emitted from the irradiation unit 4 is incident, a first reflecting surface 52A located on a side opposite to the incident surface 51 in the height direction, and a second reflecting surface 52B disposed in the width direction with respect to the first reflecting surface 52A and disposed so as to be located at a lower portion of the infusion tube 200 in the height direction. The first reflecting surface 52A and the second reflecting surface 52B are each an inclined surface having a predetermined inclination with respect to the height direction. As a result, as indicated by a solid arrow in FIG. 9, an infrared ray emitted in the height direction from the irradiation unit 4 is incident on the incident surface 51 of the light guide 5, is reflected by the first reflecting surface 52A, travels in the width direction, is reflected by the second reflecting surface 52B, travels in the height direction, and is emitted to the infusion tube 200 from a lower portion of the infusion tube 200 attached to the detection device 1D in the height direction toward the imaging unit 6. As a result, the imaging unit 6 can image transmitted light (broken line arrow) of an infrared ray emitted from a side facing the imaging unit 6 via the infusion tube 200.

The control unit 8 can evaluate a change in the outer diameter D of the infusion tube 200 in the captured image generated by the imaging unit 6 to determine whether or not the infusion tube 200 is blocked. Furthermore, the control unit 8 can evaluate a change in a light intensity distribution of transmitted light in the captured image generated by the imaging unit 6 to determine whether or not air bubbles are generated in the infusion tube 200. Specifically, the control unit 8 can determine whether or not air bubbles are generated in the infusion tube 200 from a difference in intensity of transmitted light reaching the imaging unit 6 between a case where the infusion tube 200 is filled with liquid and a case where the infusion tube 200 includes air bubbles. Therefore, even when air bubbles are generated in a part of a cross section of the infusion tube 200, the air bubbles can be more accurately detected with transmitted light passing through the infusion tube 200 and reaching the imaging unit 6.

(Infusion Pump)

Figure 10:
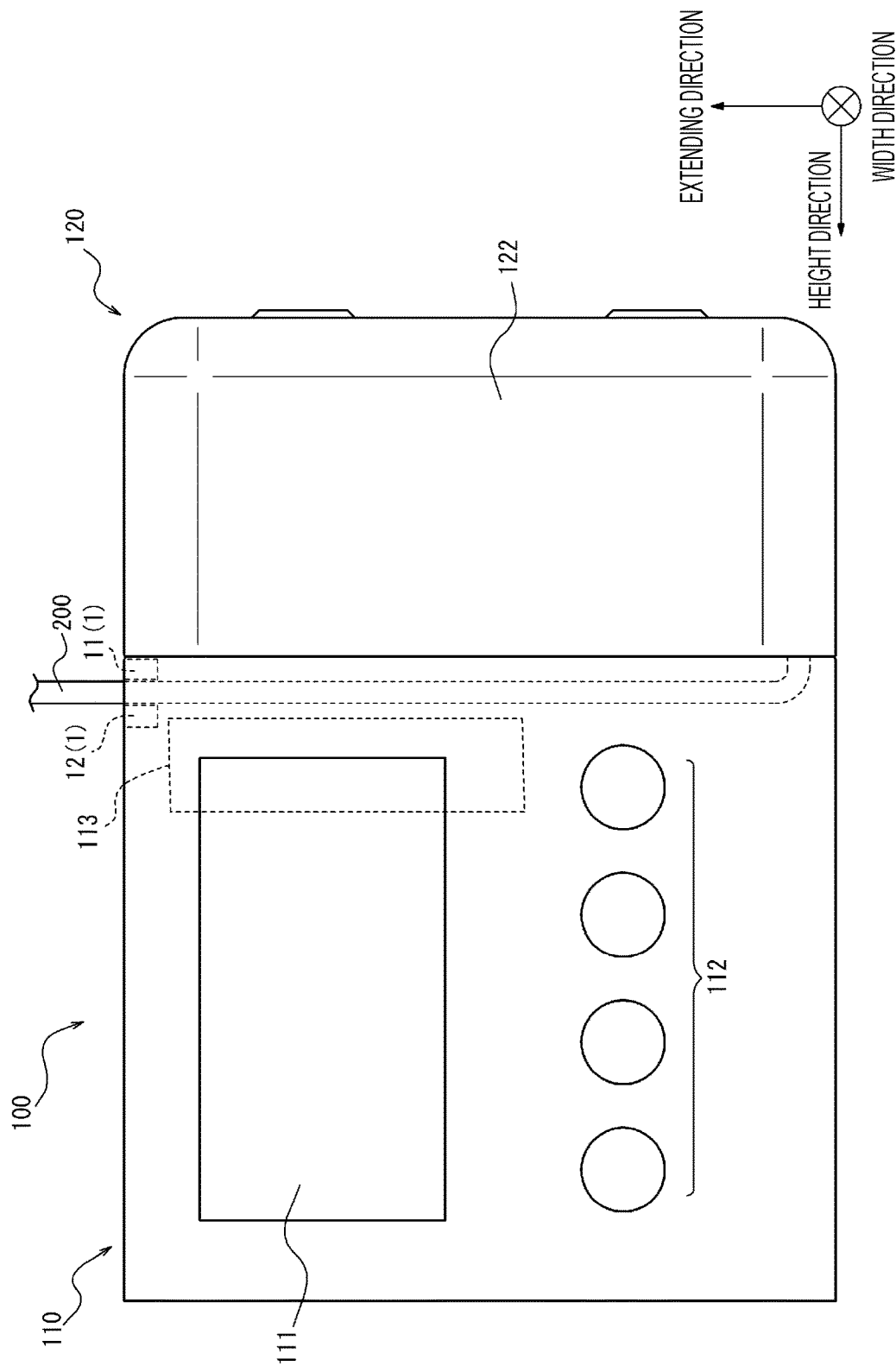
FIG. 10 is a front view illustrating a schematic configuration of an infusion pump according to an embodiment of the present disclosure.

A configuration of an infusion pump 100 according to an embodiment of the present disclosure will be described in detail with reference to FIGS. 10 and 11. Hereinafter, when the detection devices 1A, 1B, 1C, and 1D described above are not particularly distinguished from each other, they are simply collectively referred to as a detection device 1. FIG. 10 is a front view illustrating a schematic configuration of the infusion pump 100 according to the embodiment of the present disclosure. The infusion pump 100 includes the detection device 1 according to the present disclosure. As illustrated in FIG. 10, the infusion pump 100 may include a pump body 110 and an infusion cartridge 120 detachable from the pump body 110. As a result, in the infusion pump 100, the pump body 110 can be reused by replacing the disposable infusion cartridge 120. The infusion pump 100 can be used, for example, as a PCA pump, but an application thereof is not particularly limited.

As illustrated in FIG. 10, a display unit 111 on which various types of information are displayed and an operation unit 112 in which operation switches and the like are arranged are disposed on a front surface of the pump body 110. For example, a liquid feeding rate, an integrated dose, and the like are displayed on the display unit 111. Furthermore, information indicating that blockage of the infusion tube 200 or air bubbles in the infusion tube 200 have been detected by the detection device 1 is displayed on the display unit 111. The display unit 111 may be a liquid crystal screen with a touch panel used for setting a liquid feeding rate and the like. The operation unit 112 includes one or more operation switches. The operation switches disposed in the operation unit 112 are, for example, a fast delivery switch that makes liquid feeding at a liquid feeding rate higher than a set liquid feeding rate (mL/h) possible while being pressed, a start switch that starts liquid feeding by being pressed, a stop switch that forcibly stops liquid feeding by being pressed, and a power supply switch for instructing ON/OFF of power supply of the pump body 110.

Figure 11:
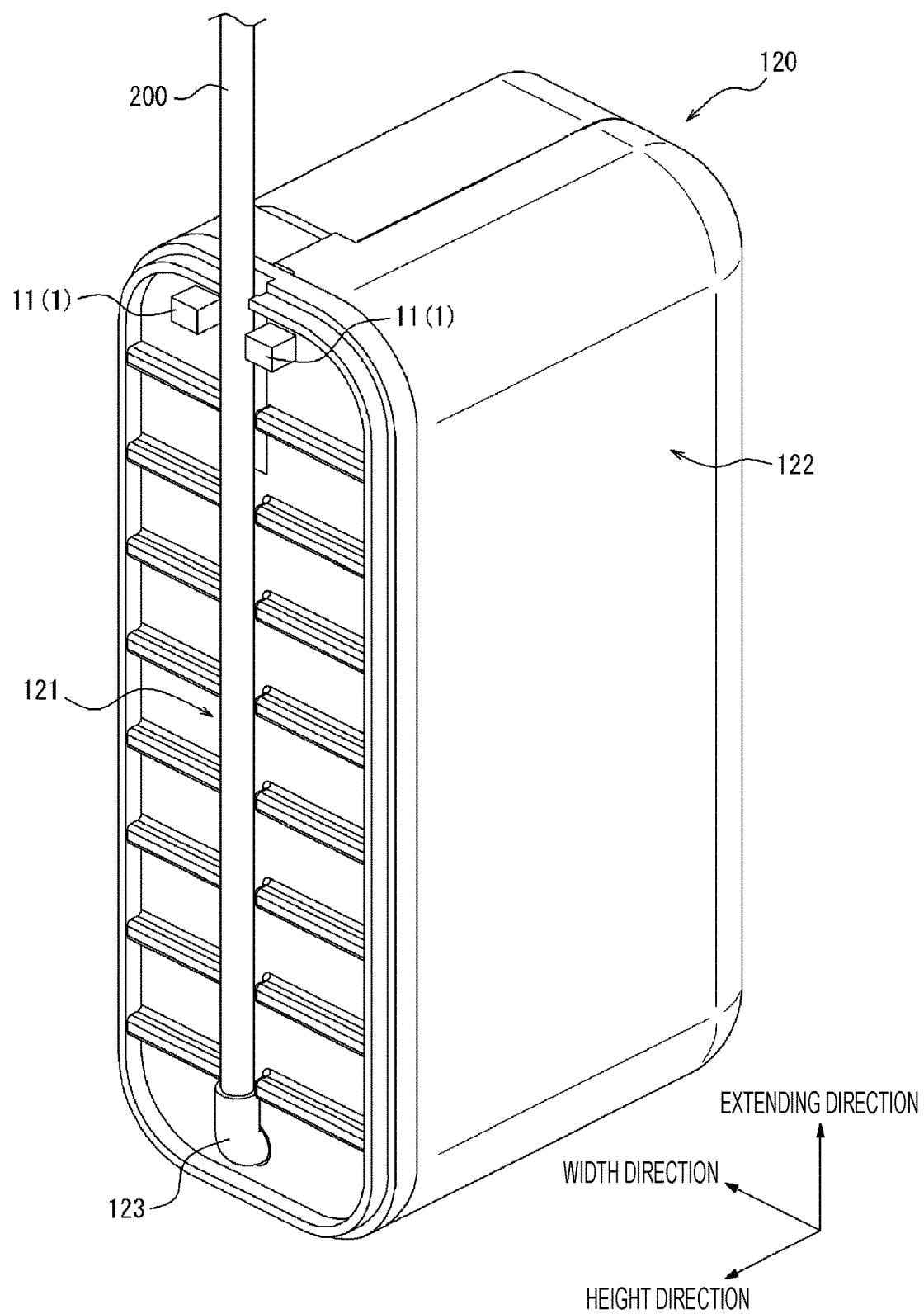
FIG. 11 is a perspective view of an infusion cartridge illustrated in FIG. 10.

FIG. 11 is a perspective view of the infusion cartridge 120 of the infusion pump 100. The infusion cartridge 120 includes a case 122 for storing an infusion pack filled with an infusion therein.

On a side of the case 122 facing the pump body 110 when being attached to the pump body 110, the infusion tube 200, a tube receiving portion 121 that receives the infusion tube 200 and sandwiches the infusion tube 200 between the tube receiving portion 121 and the pump body 110, and a filling port 123 connected to an infusion pack stored in the case 122 are formed. The tube receiving portion 121 according to the present embodiment includes a groove into which the infusion tube 200 is fitted. To the filling port 123, the infusion pack is connected from the inside of the case 122, and the infusion tube 200 is connected from the outside of the case 122. As a result, the infusion in the infusion pack stored in the case 122 can be fed to the outside via the infusion tube 200.

Referring again to FIG. 10, the pump body 110 includes a liquid feeding unit 113 that sandwiches the infusion tube 200 of the infusion cartridge 120 with the tube receiving portion 121 of the infusion cartridge 120 to be attached and feeds the infusion in the infusion tube 200 from an upstream side of the infusion tube 200 to a downstream side of the infusion tube 200. The liquid feeding unit 113 includes a plurality of fingers and a drive portion that drives the fingers. The plurality of fingers is disposed on a side surface of the pump body 110 facing the tube receiving portion 121 located on a side surface of the infusion cartridge 120. The plurality of fingers are arranged in the extending direction of the infusion tube 200. Each of the fingers is driven by the drive portion so as to reciprocate in a direction facing the tube receiving portion 121 of the infusion cartridge 120. Each of the fingers moves so as to approach the infusion cartridge 120, and the infusion tube 200 is thereby sandwiched between each of the fingers and the tube receiving portion 121. As a result, the infusion tube 200 is closed under pressure. The drive portion sequentially drives the fingers from the upstream side of the infusion tube 200 toward the downstream side of the infusion tube 200 in the extending direction of the infusion tube 200. As a result, the infusion tube 200 is sequentially closed under pressure from the upstream side of the infusion tube 200 toward the downstream side of the infusion tube 200, and peristaltically moves. Therefore, the infusion pump 100 can feed the infusion in the infusion tube 200 from the upstream side of the infusion tube 200 toward the downstream side of the infusion tube 200.

The infusion cartridge 120 includes the first housing 11 of the detection device 1. The pump body 110 includes the second housing 12 of the detection device 1 at a position facing the first housing 11 disposed in the infusion cartridge 120. In the present embodiment, the second housing 12 is disposed at a position on the downstream side of the infusion tube 200 with respect to the liquid feeding unit 113, but may be disposed on the upstream side of the infusion tube 200 with respect to the liquid feeding unit 113.

The pump body 110 and the infusion cartridge 120 are not limited to the configurations of the present embodiment. The pump body 110 and the infusion cartridge 120 may each include, for example, portions different from the above-described portions. In addition, as described above, the liquid feeding unit 113 of the pump body 110 in the present embodiment has a configuration in which the infusion tube 200 is pressed by the plurality of fingers. However, the liquid feeding unit 113 may have a different configuration as long as the infusion in the infusion tube 200 can be fed.

As described above, the detection device 1 according to the present disclosure includes: the irradiation unit 4 that emits an infrared ray toward the infusion tube 200; the imaging unit 6 configured to generate a captured image obtained by imaging the infusion tube 200 irradiated with the infrared ray by the irradiation unit 4; and the control unit 8 that detects blockage of the infusion tube 200 and air bubbles in the infusion tube 200 based on a light intensity distribution in the captured image. According to such a configuration, the detection device 1 can detect blockage of the infusion tube 200 and air bubbles in the infusion tube 200 by a single mechanism. Therefore, the detection device 1 can improve a technique for detecting abnormality of the infusion tube 200.

In the detection device 1 as an embodiment, the control unit 8 can detect blockage of the infusion tube 200 based on the outer diameter of the infusion tube 200 captured in the captured image. According to such a configuration, the detection device 1 can easily detect blockage of the infusion tube 200 based on the captured image of the infusion tube 200 captured by emitting an infrared ray.

In the detection device 1 as an embodiment, the control unit 8 can detect air bubbles in the infusion tube 200 based on the width of the region including the side wall of the infusion tube 200 captured in the captured image. According to such a configuration, the detection device 1 can easily detect air bubbles in the infusion tube 200 based on the captured image of the infusion tube 200 captured by emitting an infrared ray.

In the detection device 1 as an embodiment, the irradiation unit 4 includes the first light source 4A and the second light source 4B that emit infrared rays toward the infusion tube 200 from directions facing each other in a radial direction of the infusion tube 200, and the control unit 8 can detect blockage of the infusion tube 200 and air bubbles in the infusion tube 200 based on a captured image obtained by imaging the infusion tube 200 in a state in which the infrared rays are emitted from both the first light source 4A and the second light source 4B. According to such a configuration, the detection device 1 can irradiate the infusion tube 200 with infrared rays from two directions facing each other to more clearly image the infusion tube 200 as compared with a case where the infusion tube 200 is irradiated with an infrared ray from one direction. As a result, the detection device 1 can more accurately detect abnormality of the infusion tube 200.

In the detection device 1 as an embodiment, the irradiation unit 4 includes a plurality of light sources that emits infrared rays toward the infusion tube 200 from different directions, and the control unit 8 can detect blockage of the infusion tube 200 and air bubbles in the infusion tube 200 based on a plurality of captured images obtained by imaging the infusion tube 200 in a state in which the infrared rays are emitted from different light sources. According to such a configuration, the detection device 1 can irradiate the infusion tube 200 with infrared rays from various directions to image the infusion tube 200. As a result, the detection device 1 can more accurately detect abnormality of the infusion tube 200.

The detection device 1 as an embodiment further includes the contact portion 3 that comes into contact with the infusion tube 200 from both sides of the infusion tube 200 in the radial direction at two locations spaced apart from each other in the extending direction of the infusion tube 200, and the control unit 8 can detect blockage of the infusion tube 200 and air bubbles in the infusion tube 200 based on a light intensity distribution between the two locations in the extending direction of the infusion tube 200 captured in the captured image. According to such a configuration, the detection device 1 can easily change the shape of the infusion tube 200 between the two locations in contact with the contact portion 3 of the infusion tube 200 in the extending direction. Therefore, the detection device 1 can more accurately detect abnormality.

The infusion pump 100 according to the present disclosure includes the detection device 1 described above. According to such a configuration, the infusion pump 100 can detect blockage of the infusion tube 200 and air bubbles in the infusion tube 200 by a single mechanism. Therefore, the infusion pump 100 can improve a technique for detecting abnormality of the infusion tube 200.

Although the present disclosure has been described with reference to the drawings and examples, it should be noted that those skilled in the art can make various variations and modifications based on the present disclosure. Therefore, it should be noted that these variations and modifications fall within the scope of the present disclosure. For example, functions and the like included in each means, each step, or the like can be rearranged so as not to be logically inconsistent, and a plurality of means, steps, and the like can be combined into one or divided.

For example, in the above-described embodiments, the detection device 1 has been described as including the first housing 11 and the second housing 12, in which the receiving plate 2, the contact portion 3, and the light guide 5 are disposed in the first housing 11, and the irradiation unit 4, the imaging unit 6, the output unit 7, and the control unit 8 are disposed in the second housing 12. However, in the detection device 1, all of the above-described components may be disposed in one housing. This makes it possible to manufacture the detection device 1 by a simpler manufacturing method, and to suppress manufacturing cost. Alternatively, at least one of the components described as being disposed in the first housing 11 or the second housing 12 may be disposed in the other housing.

Alternatively, in the above-described embodiments, the detection device 1 has been described as including the light guide 5. However, when the irradiation unit 4 is disposed at a position where the irradiation unit 4 can directly irradiate the infusion tube 200 attached to the detection device 1 with an infrared ray, the light guide 5 may be omitted. This makes it possible to manufacture the detection device 1 by a simpler manufacturing method, and to suppress manufacturing cost.

Alternatively, in the above-described embodiments, the detection device 1 has been described as including the receiving plate 2, the contact portion 3, the irradiation unit 4, the light guide 5, the imaging unit 6, the output unit 7, and the control unit 8. However, at least one of these components may be provided by the infusion pump 100 on which the detection device 1 is mounted. That is, the detection device 1 according to the present disclosure may be the infusion pump 100 itself. For example, the control unit 8 of the detection device 1 may be a control device included in the infusion pump 100. Specifically, a program describing processing contents executed by the control unit 8 of the detection device 1 according to an embodiment can be stored in a memory of the control device of the infusion pump 100, and the program can be read and executed by a processor of the control device of the infusion pump 100. Alternatively, the output unit 7 of the detection device 1 may be the display unit 111 included in the infusion pump 100.

Alternatively, in the above-described embodiments, the thresholds $D_A$ and $D_B$ for blockage detection and the thresholds $W1_A$ and $W2_A$ for air bubble detection have been described as being constants. However, these values may be variables that can vary depending on the temperature of an environment in which the detection device 1 is used. In such a case, the control unit 8 of the detection device 1 may store a correspondence relationship between the temperature of the environment and thresholds of blockage detection and air bubble detection, and set the above-described thresholds when performing abnormality detection. As a result, the detection device 1 can more accurately detect abnormality of the infusion tube 200 in consideration of factors that vary depending on the temperature of the environment, such as an expansion ratio of the infusion tube 200.

REFERENCE CHARACTER LIST 1 (1A, 1B, 1C, 1D) Detection device
11 First housing
12 Second housing
2 Receiving plate
3 Contact portion
3A First contact portion
3B Second contact portion
4 (4A, 4B, 4C, 4D) Irradiation unit (light source)
5 (5A, 5B) Light guide
51 Incident surface
52 (52A, 52B) Reflecting surface
6 Imaging unit
7 Output unit
8 Control unit
81 Memory
82 Processor
100 Infusion pump
110 Pump body
111 Display unit
112 Operation unit
113 Liquid feeding unit
120 Infusion cartridge
121 Tube receiving portion
122 Case
123 Filling port
200 Infusion tube
R (R1, R2) High light intensity region
D ($D_0$) Outer diameter
$D_A$, $D_B$ Threshold of blockage detection
W (W1, W2, $W1_0$, $W2_0$) Width
$W1_A$, $W2_A$ Threshold of air bubble detection

The invention claimed is:

1. A detection device comprising:
an irradiation unit configured to emit an infrared ray toward an infusion tube;
an imaging unit configured to generate a captured image obtained by imaging the infusion tube irradiated with the infrared ray by the irradiation unit; and
a control unit configured to:
determine a light intensity value of each pixel included in the captured image,
specify high light intensity regions having a light intensity value equal to or more than a predetermined threshold as regions including opposing side wall portions of the infusion tube captured in the captured image based on a light intensity distribution in the captured image, and
detect blockage of the infusion tube and air bubbles in the infusion tube based on the specified high light intensity regions.

2. The detection device according to claim 1, wherein the control unit is configured to detect blockage of the infusion tube based on an outer diameter of the infusion tube captured in the captured image.

3. The detection device according to claim 1, wherein the control unit is configured to detect air bubbles in the infusion tube based on a width of at least one of the high light intensity regions.

4. The detection device according to claim 1, wherein:
the irradiation unit comprises a first light source and a second light source configured to emit infrared rays toward the infusion tube from directions facing each other in a radial direction of the infusion tube; and
the control unit is configured to detect blockage of the infusion tube and air bubbles in the infusion tube based on a captured image obtained by imaging the infusion tube in a state in which the infrared rays are emitted from both the first source and second light source.

5. The detection device according to claim 1, wherein:
the irradiation unit comprises a plurality of light sources configured to emit infrared rays toward the infusion tube from different directions; and the control unit is configured to detect blockage of the infusion tube and air bubbles in the infusion tube based on a plurality of captured images obtained by imaging the infusion tube in a state in which the infrared rays are emitted from different light sources.

6. The detection device according to claim 1, further comprising:
a contact portion that contacts the infusion tube from both sides of the infusion tube in a radial direction at two locations spaced apart from each other in an extending direction of the infusion tube; wherein:
the control unit is configured to detect blockage of the infusion tube and air bubbles in the infusion tube based on a light intensity distribution between the two locations in the extending direction of the infusion tube captured in the captured image.

7. The detection device according to claim 2, wherein the control unit is configured to determine that the infusion tube is blocked when a change in the outer diameter of the infusion tube from an initial outer diameter to a determined current outer diameter is outside a predetermined range.

8. The detection device according to claim 3, wherein the control unit is configured to determine that an air bubble is in the infusion tube when a change in a width of at least one of the high intensity regions is outside a predetermined range.

9. The detection device according to claim 3, wherein the control unit is configured to determine that an air bubble is in the infusion tube when a change in a width of a first of the high intensity regions is outside a first predetermined range and a change in a width of a second of the high intensity regions is outside a second predetermined range.

10. An infusion pump comprising:
a detection device comprising:
an irradiation unit configured to emit an infrared ray toward an infusion tube,
an imaging unit configured to generate a captured image obtained by imaging the infusion tube irradiated with the infrared ray by the irradiation unit, and
a control unit configured to:
determine a light intensity value of each pixel included in the captured image,
specify high light intensity regions having a light intensity value equal to or more than a predetermined threshold as regions including opposing side wall portions of the infusion tube captured in the captured image based on a light intensity distribution in the captured image, and
detect blockage of the infusion tube and air bubbles in the infusion tube based on the specified high light intensity regions.

11. The infusion pump according to claim 10, further comprising:
a pump body; and
an infusion cartridge that is detachable from the pump body.

12. A detection device comprising:
one or more infrared ray light emitting diodes configured to emit an infrared ray toward an infusion tube;
an image sensor configured to generate a captured image obtained by imaging the infusion tube irradiated with the infrared ray by the one or more infrared ray light emitting diodes; and
a control unit comprising a memory and a processor and configured to;
determine a light intensity value of each pixel included in the captured image,
specify high light intensity regions having a light intensity value equal to or more than a predetermined threshold as regions including opposing side wall portions of the infusion tube captured in the captured image based on a light intensity distribution in the captured image, and
detect blockage of the infusion tube and air bubbles in the infusion tube based on the specified high light intensity regions.

13. The detection device according to claim 12, wherein the control unit is configured to detect blockage of the infusion tube based on an outer diameter of the infusion tube captured in the captured image.

14. The detection device according to claim 12, wherein the control unit is configured to detect air bubbles in the infusion tube based on a width of at least one of the high light intensity regions.

15. The detection device according to claim 12, wherein:
the one or more infrared ray light emitting diodes comprises a first infrared ray light emitting diode and a second infrared ray light emitting diode configured to emit infrared rays toward the infusion tube from directions facing each other in a radial direction of the infusion tube; and
the control unit is configured to detect blockage of the infusion tube and air bubbles in the infusion tube based on a captured image obtained by imaging the infusion tube in a state in which the infrared rays are emitted from both the first light source and the second light source.

16. The detection device according to claim 12, wherein:
the one or more infrared ray light emitting diodes comprises a plurality of infrared ray light emitting diodes configured to emit infrared rays toward the infusion tube from different directions; and
the control unit is configured to detect blockage of the infusion tube and air bubbles in the infusion tube based on a plurality of captured images obtained by imaging the infusion tube in a state in which the infrared rays are emitted from different infrared ray light emitting diodes.

17. The detection device according to claim 12, further comprising:
a contact portion that contacts the infusion tube from both sides of the infusion tube in a radial direction at two locations spaced apart from each other in an extending direction of the infusion tube; wherein:
the control unit is configured to detect blockage of the infusion tube and air bubbles in the infusion tube based on a light intensity distribution between the two locations in the extending direction of the infusion tube captured in the captured image.

* * * * *